(12) United States Patent
Pleva

(10) Patent No.: US 7,939,107 B2
(45) Date of Patent: May 10, 2011

(54) EMU OIL AND FRUIT COMPOSITION

(76) Inventor: Raymond M. Pleva, Cedar, MI (US)

( * ) Notice: Subject to any disclaimer, the term of this patent is extended or adjusted under 35 U.S.C. 154(b) by 76 days.

(21) Appl. No.: 12/486,327

(22) Filed: Jun. 17, 2009

(65) Prior Publication Data

US 2009/0258080 A1    Oct. 15, 2009

Related U.S. Application Data

(63) Continuation of application No. 11/572,851, filed as application No. PCT/US2005/026782 on Jul. 28, 2005, now abandoned.

(60) Provisional application No. 60/521,965, filed on Jul. 28, 2004.

(51) Int. Cl.
*A61K 35/12* (2006.01)
*A61K 36/736* (2006.01)

(52) U.S. Cl. .......................... 424/522; 424/735; 514/558

(58) Field of Classification Search .................. None
See application file for complete search history.

(56) References Cited

U.S. PATENT DOCUMENTS

| | | | |
|---|---|---|---|
| 5,472,713 A | 12/1995 | Fein et al. | |
| 5,662,921 A | 9/1997 | Fein et al. | |
| 5,670,200 A | 9/1997 | Pleva | |
| 6,103,246 A | 8/2000 | Tisdale et al. | |
| 6,342,208 B1 | 1/2002 | Hyldgaard et al. | |
| 6,407,141 B1 | 6/2002 | Hart | |
| 6,531,126 B2 | 3/2003 | Farmer | |
| 6,534,086 B1 | 3/2003 | Krumhar | |
| 6,579,543 B1 | 6/2003 | McClung | |
| 6,733,751 B2 | 5/2004 | Farmer | |
| 6,773,718 B2* | 8/2004 | Seth et al. ...................... 424/443 |
| 6,881,776 B2* | 4/2005 | Butuc ........................... 524/284 |
| 7,666,859 B2* | 2/2010 | Turkowitz ..................... 514/171 |
| 2002/0055562 A1 | 5/2002 | Butuc | |
| 2003/0031724 A1 | 2/2003 | Orthoefer et al. | |
| 2003/0175332 A1 | 9/2003 | Brown et al. | |
| 2005/0123479 A1 | 6/2005 | Ferrante | |
| 2005/0266064 A1 | 12/2005 | McCarthy | |
| 2006/0073211 A1* | 4/2006 | Marenick et al. ............. 424/581 |
| 2006/0105059 A1* | 5/2006 | McArthur ..................... 424/725 |
| 2008/0073211 A1* | 3/2008 | Cernasov ...................... 204/450 |

FOREIGN PATENT DOCUMENTS

| | | |
|---|---|---|
| WO | 98/50005 | 11/1998 |
| WO | 00/26285 | 5/2000 |
| WO | 01 13956 A2 | 3/2001 |
| WO | 03/043590 | 5/2003 |
| WO | 2008 016823 A2 | 2/2008 |

OTHER PUBLICATIONS

Internet article obtained from Lazy S Farm (www.lazysfarm.com) entitled "Skin Care," retrieved Nov. 6, 2005 08:14:22 GMT. Copyright 1999-2001.
Internet article obtained from www.todieforsoap.com entitled "Balms & Butters," retrieved Nov. 12, 2005 20:11:11 GMT.
Internet article obtained from www.sunsetloft.com entitled "Sunset Loft Bath Shoppe," retrieved Nov. 8, 2005 14:21:55 GMT. Copyright 2003-2004.

* cited by examiner

*Primary Examiner* — Christopher R. Tate
(74) *Attorney, Agent, or Firm* — McGarry Bair PC

(57) ABSTRACT

A composition is provided comprising emu oil and processed whole fruit. The composition is in a form for either topical application to human skin or for internal ingestion.

6 Claims, No Drawings

EMU OIL AND FRUIT COMPOSITION

CROSS-REFERENCE TO RELATED APPLICATION

This application is a continuation of U.S. application Ser. No. 11/572,851, filed Jan. 29, 2007, which claims priority on International Application No. PCT/US2005/026782, filed Jul. 28, 2005, which claims the benefit of U.S. Provisional Patent Application No. 60/521,965, filed Jul. 28, 2004, both of which are incorporated herein in their entirety.

BACKGROUND OF THE INVENTION

1. Field of the Invention

The invention relates to compositions suitable for topical application to human skin and suitable for ingesting, and, more particularly, to natural compositions comprising emu oil and various fruits.

2. Description of the Related Art

Emu oil (also known as kalaya oil) is rendered from the bird's fat. It is used in cosmetics and cosmetic related items, including wrinkle retarding emollients, cosmetic bases and moisturizers for the face and body. It exhibits certain surface penetrating characteristics that can increase the penetration of compositions through human skin. It is therapeutically used in methods for lowering cholesterol, triglycerides and low density lipoproteins and increasing high density lipoproteins. It is believed by many to prevent and treat allergies, prevent scarring, treat headaches, prevent nosebleeds, treat cold and flu symptoms, and relieve discomfort associated with menstruation. It is known to be ingested by spoon, dropper, tablet, gelatin capsule, time release capsules, and as a food additive. It can be administered in the form of emulsions, suspensions, and powders. Topically, it can be administered in creams, lotions, oils, powders, and gels.

Some fruits are known to be high in anti-oxidants and have proven effective in improving health. Blueberries, pomegranates, plums, cranberries, black chokeberries (*sanbucus nigra*), black elderberries, and cherries are all relatively high in anti-oxidants.

Consumption of cherries and its products are known to provide a variety of additional health benefits. Tart cherries (*prunus cerasus*), especially the Montmorency and Balaton varieties, have been shown to be a particularly good source of bioflavonoids in addition to anti-oxidants. For example, anthocyanins from cherries are known to be an effective anti-inflammatory agent. Melatonins from cherries are known to be an effective anti-oxidant. Both have been found to reduce cancers. Cherries are also believed to assist in the proper balancing of certain hormones. Indeed, cherries are commonly called "the healing fruit."

It is known to extract components from cherries and utilize them in other compositions such as food additives and supplements. For example, flavonoids have been extracted from tart cherries and incorporated into foods. It is also known to combine alpha-hydroxy acids with emu oil to provide moisturizing creams and lotions. Cherries are known to be a source of malic acid which is a type of alpha-hydroxy acid. Also, it is known to combine pitted tart cherries with comminuted meat to increase moisture, reduce fat content, and improve flavor. However, the full benefits of fruits and emu oil have yet to be realized.

SUMMARY OF THE INVENTION

According to the invention, more of the benefits of emu oil and fruits can be realized by a composition comprising emu oil and processed whole fruit, preferably a fruit selected from the group including blueberries, pomegranates, plums, cranberries, black chokeberries, black elderberries, and cherries. In one aspect, the composition includes emu oil and whole cherries or at least one substance extracted from whole cherries. The substance is from the group consisting of anthocyanins, melatonins, phenolics, and flavonoids.

DETAILED DESCRIPTION

The following description primarily addresses a preferred embodiment of the present invention. Those skilled in the article readily recognize, however, that the invention may be satisfactorily employed in other applications, and that alternative aspects and embodiments of the invention are possible. All those other applications, aspects and embodiments of the invention are hereby expressly included in, and form a part of, the invention.

The invention comprises a composition formed of emu oil and fruit. Preferably, the emu oil is processed in that it is refined to remove impurities, discoloration, etc. A preferred process for refining emu oil is commonly termed "cold rendering" in which the temperature of the oil is not raised too high so as to make it unstable. A preferred emu oil for use in the present invention can be obtained from L. B. Processors LLC, 1846 Mosley Ferry Rd., Chapmansboro, Tenn. 37035. It is believed that any other emu oil having a similar composition is substantially equally effective for purposes of the invention.

A preferred fruit includes cherries, and preferably tart cherries of the Montmorency or Balaton varieties. Sweet cherries can also provide similar benefits. The cherries are preferably provided in the form of a cherry concentrate. The cherry concentrate is made in a conventional manner by squeezing and cooking down whole cherries preferably to a concentration of 68 brix. The term "brix" is used in its conventional meaning of a unit of measure of sucrose (the percent of sugar in 100 g of cane sugar solution). A concentration greater or lesser than 68 brix is acceptable, preferably within a range of plus or minus seven brix. Using Montmorency cherries, it takes about 88 lbs. of cherries to render 1 gallon of cherry concentrate. Cherry concentrates within the preferred range of concentration are commercially available.

Another preferred form of cherries is a freeze dried powder manufactured by a vacuum freeze drying process. A commercial source of freeze dried red tart cherry powder is Crystals International, Inc., 600 West Dr. M. L. King, Jr. Blvd., Plant City, Fla. This product contains 70% red Tart cherry juice concentrate. Cherry powder can also be made in spray dry, drum dry and pan dry processes. Other acceptable forms of cherries include cherry purees and Elliott cherries (similar to a puree, but with bigger pieces of whole cherries).

In one form, the emu oil and cherries are combined to form a cream, oil, or lotion for topical use on human skin. A preferred composition will include a range of 1% to 20% emu oil, and 2% to 15% cherries, by weight. All of the natural health benefits of the cherries such as those found in specified compounds including anthocyanins and melatonins are transported subcutaneously by the emu oil's penetration of the skin. It may be advisable to provide other compounds in the composition to enhance solubility and viscosity characteristics. Such compounds might include water, glycerin, and well known emulsions that are common to cosmetics, creams and oils.

In another form, emu oil and cherries are reduced to a form for internal administration. One example is an oral administration comprising a gelatin capsule of the composition. Other examples include a powdered form of composition in a capsule, or a dried form of the composition pressed into a tablet. A preferred composition for oral administration will include a range of 1% to 35% emu oil, and 1% to 45% cherries, by weight. In liquid form, the composition can be administered systemically such as by subcutaneous or intramuscular injection. It can also be administered orally by solution, or emulsion with fewer side effects.

It is believed that the composition improves digestion, retards the aging process, reduces the inflammation of arthritis and gout, protects against certain types of cancer and heart disease, assists in stabilizing and balancing hormones, neutralizes free radicals, reduces short-term memory loss, aids in combating stress, reduces high strain and fatigue, reduces LDL cholesterol, improves the bodies of certainty in rhythms and natural sleep patterns, and maintains a long, stable shelf life, all without disruptive side effects. The invention also encompasses compositions comprising emu oil and active ingredients extracted from whole cherries, such as cherry-derived anthocyanins and melatonins.

It will be apparent that the composition can take the form of creams, pills, gelatin capsules, massage oils, lotions, gels, shampoos, soaps, conditioners, sprays, solids, and powders. It is believed that with certain emulsions well known to those of ordinary skill in the art, such products as car cleaners and floor cleaners can benefit from the composition. As well, it is believed that pet food can be enhanced by incorporating a combination of emu oil and fruit.

Of course other fruits can be used in combination with emu oil for the particular benefits afforded by those fruits. For example, fruits known to be high in anti-oxidants have proven effective. Blueberries, pomegranates, plums, cranberries, black chokeberries (sanbucus nigra), and black elderberries in concentrate form, in extracts, or in powders can be used instead of cherries. But they can also be used in addition to cherries.

It is believed that the addition of other ingredients can enhance the benefits of the composition. The addition of coenzyme Q10 has also been shown to aid with heart disease, brain diseases and periodontal diseases. A sample formula will contain one part cherry concentrate, one part emu oil, one part omega 3 fish oil (pharmaceutical grade/toxin free), one part certified organic top grade flaxseed oil, and one part CoQ10. If taste must be enhanced, more cherry concentrate can be added.

While the invention has been specifically described in connection with certain specific embodiments thereof, it is to be understood that this is by way of illustration and not of limitation, and the scope of the appended claims should be construed as broadly as the prior art will permit.

What is claimed is:

1. A composition comprising emu oil in an amount of 1% to 35% by weight, processed whole cherries in an amount of 1 to 45%, by weight, and omega-3 fish oil.

2. The composition of claim 1, wherein the emu oil is in an amount of 1 to 20% by weight, and the processed whole cherries are in an amount of 2 to 15% by weight.

3. The composition of claim 1, wherein the composition is in a form selected from the group consisting of a solid, powder, pill, gelatin capsule, cream, massage oil, lotion, gel, shampoo, soap, conditioners, and spray.

4. The composition of claim 1, wherein the processed whole cherries are processed into the form of cherry powder.

5. The composition of claim 1, wherein the processed whole cherries are processed into the form of cherry concentrate.

6. A composition comprising one part cherry concentrate processed from whole cherries, one part emu oil, one part omega-3 fish oil, one part flaxseed oil, and one part coenzyme Q10.

* * * * *